(12) United States Patent
Ott et al.

(10) Patent No.: US 7,858,942 B2
(45) Date of Patent: Dec. 28, 2010

(54) METHOD AND DEVICE FOR MONITORING WALL THICKNESS

(75) Inventors: Armin Ott, Riekofen (DE); Stefan Piana, Köfering (DE); Christian Detrois, Lappersdorf (DE)

(73) Assignee: Krones AG, Neutraubling (DE)

( * ) Notice: Subject to any disclaimer, the term of this patent is extended or adjusted under 35 U.S.C. 154(b) by 0 days.

(21) Appl. No.: 11/997,376

(22) PCT Filed: Jul. 5, 2006

(86) PCT No.: PCT/EP2006/006525
§ 371 (c)(1),
(2), (4) Date: Sep. 2, 2008

(87) PCT Pub. No.: WO2007/014611
PCT Pub. Date: Feb. 8, 2007

(65) Prior Publication Data
US 2009/0010385 A1    Jan. 8, 2009

(30) Foreign Application Priority Data
Aug. 3, 2005 (DE) .................. 10 2005 037 101

(51) Int. Cl.
*G01B 15/02* (2006.01)
(52) U.S. Cl. .................................. 250/358.1
(58) Field of Classification Search .......... 250/358.1
See application file for complete search history.

(56) References Cited

U.S. PATENT DOCUMENTS

| | | |
|---|---|---|
| 2,685,816 A | 8/1954 | Hortenstine |
| 3,439,178 A | 4/1969 | Rottman |
| 3,449,546 A | 6/1969 | Dhoble |
| 3,456,788 A | 7/1969 | Stapf et al. |
| 3,721,501 A | 3/1973 | Atkinson et al. |
| 3,729,632 A | 4/1973 | Cho et |
| 3,827,812 A | 8/1974 | Heimann |

(Continued)

FOREIGN PATENT DOCUMENTS

DE    3611536    10/1987

(Continued)

OTHER PUBLICATIONS

EPO English Translation of DE10116665.*

(Continued)

*Primary Examiner*—David P Porta
*Assistant Examiner*—Djura Malevic
(74) *Attorney, Agent, or Firm*—Marshall, Gerstein & Borun LLP

(57) ABSTRACT

A method for detecting the wall thickness of a container such as a bottle made of PET, for example, in which the absorption of radiation along a first and a second test path of the measurement radiation is ascertained, whereby the test paths intersect the container at two points of intersection such that the two test paths have at least one point of intersection approximately in common. Further, a method for detecting the wall thickness of a container such as a bottle made of PET, for example, such that the wall thickness is detected in the transitional area of a side wall of the container to a bottom area of the container.

13 Claims, 2 Drawing Sheets

U.S. PATENT DOCUMENTS

| | | | |
|---|---|---|---|
| 3,980,890 A | | 9/1976 | Heckrodt et al. |
| 4,304,995 A | | 12/1981 | Huttunen et al. |
| 4,393,305 A | | 7/1983 | Shimizu et al. |
| 4,429,225 A | | 1/1984 | Fumoto et al. |
| 4,578,874 A | | 4/1986 | Juengel |
| 4,831,258 A | | 5/1989 | Paulk et al. |
| 5,139,406 A | * | 8/1992 | Hoshino et al. ............. 425/140 |
| 5,291,271 A | * | 3/1994 | Juvinall et al. .............. 356/632 |
| 5,444,237 A | * | 8/1995 | Takizawa ................ 250/223 B |
| 5,536,935 A | * | 7/1996 | Klotzsch et al. ......... 250/223 B |
| 5,574,288 A | | 11/1996 | Harklau et al. |
| 5,712,926 A | | 1/1998 | Eberhard et al. |
| 5,902,526 A | | 5/1999 | Davis et al. |
| 6,188,079 B1 | * | 2/2001 | Juvinall et al. ......... 250/559.27 |
| 6,192,101 B1 | | 2/2001 | Grodzins |
| 6,863,860 B1 | * | 3/2005 | Birckbichler et al. ....... 264/410 |
| 6,985,221 B2 | | 1/2006 | Semersky et al. |
| 7,253,892 B2 | | 8/2007 | Semersky et al. |
| 7,271,893 B2 | * | 9/2007 | Seethaler ................. 356/239.6 |
| 7,595,870 B2 | * | 9/2009 | Ringlien .................. 356/239.4 |
| 2003/0223086 A1 | * | 12/2003 | Semersky et al. ........... 356/630 |
| 2006/0208172 A1 | * | 9/2006 | Akkerman et al. ...... 250/223 B |

FOREIGN PATENT DOCUMENTS

| | | |
|---|---|---|
| DE | 39 30 828 A1 | 3/1991 |
| DE | 10116665 | 10/2002 |
| EP | 0348524 | 6/1995 |
| EP | 1348932 | 1/2003 |
| FR | 2544856 | 10/1984 |
| GB | 2 178 361 A | 2/1987 |
| JP | 56-28830 A | 3/1981 |
| JP | 06138064 | 5/1994 |
| JP | 09318559 | 12/1997 |
| WO | WO-84/02874 A1 | 8/1984 |
| WO | WO-2007/014611 | 2/2007 |

OTHER PUBLICATIONS

JPO English Translation of JP09318559A.*
International Preliminary Report on Patentability; International Filing Date: Jul. 5, 2006; Date of Issuance: Feb. 26, 2008.
EPO Published comments of Applicants with respect to Reference 1-7 in European Opposition of EP Pat. No. 1,279,002. Applicants' comments were filed with the EPO Sep. 28, 3006 and promptly published thereafter.
EPO Published comments of Applicants with respect to Reference 8 in European Opposition of EP Pat. No. 1,279,002 filed. Applicants' comments were filed with the EPO on Feb. 9, 2009 and promptly published thereafter (translation included).
Liptak, Instrument Engineers' Handbook: Process Control and Optimization, 4th ed., pp. 100 (2003).
Translation of Second Office Action of the Chinese Patent Office, dated Sep. 1, 2010, in corresponding Chinese Patent Application No. 200680028571.X.

* cited by examiner

METHOD AND DEVICE FOR MONITORING WALL THICKNESS

CROSS-REFERENCE TO RELATED APPLICATION

The present application claims the benefit of priority of International Patent Application No. PCT/EP2006/006525, filed on Jul. 5, 2006, which application claims priority of German Patent Application No. 10 2005 037 101.9, filed Aug. 3, 2005. The entire text of the priority application is incorporated herein by reference in its entirety.

FIELD OF THE DISCLOSURE

The disclosure relates to a method and a device for detecting the wall thickness of a container, and particularly to the wall thickness of a bottle, for example, such as the wall thickness of a plastic bottle made of PET as used for testing of bottles to ascertain whether they have been manufactured properly.

BACKGROUND

EP 1 348 932 A2 describes a method and a device with which a beam of light is passed through the bottle in a direction perpendicular to the axis of the bottle to thereby ascertain the wall thickness based on the measured absorption of radiation. This may be done at various heights along the bottle.

DE 101 16 665 A1 describes a method for controlling a blow-molding operation in which the wall thickness of a container is detected immediately after it is produced and then is compared with an ideal wall thickness so the manufacturing process is subsequently adapted to obtain the smallest possible differences between the actual wall thickness and the ideal wall thickness.

With this method and device, it has been found that definitive bottles cannot always be detected reliably.

SUMMARY OF THE DISCLOSURE

Therefore, one object of the present disclosure is to improve upon the method and the device.

The method known from the prior art is essentially suitable for ascertaining the wall thickness in the area of the smooth side wall. This makes use of the fact that the side wall is of approximately equal thickness at the two locations where radiation is absorbed. When this is not the case, this method cannot be used.

Due to the arrangement of two test paths, which have a common point of intersection, however, the absorption through a point of intersection can be determined by measurement with the other test path. For a test path that passes through areas of the container of different wall thicknesses, the absorption contribution of the shared point of intersection cannot be taken into account. It is therefore possible to ascertain the wall thickness at various locations on the container, i.e., including those where it cannot be assumed that the wall thickness should be the same.

It has been found that the wall thickness is approximately the same at the same height of the bottle so that a test path has two points of intersection at approximately the same height so that the wall thickness can easily be ascertained at the common point of intersection.

It has also been found that in the lower corners/rounded areas of the bottle, the wall thickness may be very thin and testing this area is especially suitable for detecting defectively manufactured bottles. A test path will thus usually have a point of intersection preferably in the transition area of the side-wall area with the bottom area of the container.

To determine the wall thickness in this area, which may be relatively low, it is therefore now advantageously possible to use the wall thickness at the common point of intersection to calculate the wall thickness in the transitional area. This may be done by calculation, but in principle it would also be possible, e.g., by differential measurement of the measured absorption.

The two test paths may form different angles, the upper and lower limits of which are defined in the claims.

An angle between 40° and 50°, i.e., an angle of approximately 45° has proven to be especially suitable.

As the radiation whose absorption is ascertained, any type of electromagnetic radiation that is absorbed by the container wall may be used. For example, this may include infrared radiation, visible radiation, UV radiation, terahertz radiation, X-ray radiation or a low-energy ionizing radiation that can be generated from X-ray tubes at less than 5 keV and is not subject to the approval requirement for X-rays. Radioactive radiation or other particulate radiation may also be used here to ascertain the wall thickness.

It is also possible to use two different types of radiation such as particulate radiation and electromagnetic radiation or two types of radiation having different wavelengths. Therefore, the accuracy of the measurement can be increased, in particular when there is a high absorption by the material of the container at least at one of the wavelengths.

The wall thicknesses thereby ascertained are advantageously used to regulate and/or control the container manufacturing process according to DE 101 16 665 A1. Reference is herewith made to the procedures disclosed in DE 101 16 665 A1 to the full extent.

The values thereby ascertained for the wall thickness of individual bottles may also be assigned unambiguously to the blow-molding molds involved in the manufacturing process and to the holding mandrels that transport the blanks for the bottles through a heating zone, this assignment being made by a control unit in combination with the machine rotary transducer to be able to detect deviations and/or malfunctions of individual blow-molding molds and be able to perform individual optimization of the manufacturing parameters such as blow-molding pressures, drawing rates or temperature profiles of the blanks.

For especially reliable detection of containers not produced properly, this method detects the wall thickness in the area of the container where the side-wall area develops into the bottom area. As it has been found, the lowest wall thicknesses, i.e., the areas that are especially critical, are usually located in this transitional area.

The device for determining the wall thickness of the container has two test paths. The absorption of the radiation can be determined along these test paths. The test paths intersect a container position at two intersection points. The device is characterized in that the test paths have in common approximately at least one point of intersection.

With this method as well as with this device, it is not absolutely necessary for the test paths to have exactly the same point of intersection, but instead it is sufficient if they are at least so close together that there is no significant change in thickness of the container wall between the two points of intersection or none is to be expected.

The device for detecting the wall thickness of a container is designed so that the wall thickness in the transition area of a side-wall area of the container to a bottom area of the container can be detected. This makes it possible to reliably detect bottles that have not been manufactured properly.

BRIEF DESCRIPTION OF THE DRAWINGS

A preferred embodiment of the disclosure is explained on the basis of the accompanying figures, in which.

DETAILED DESCRIPTION OF THE PREFERRED EMBODIMENTS

Figure 1:
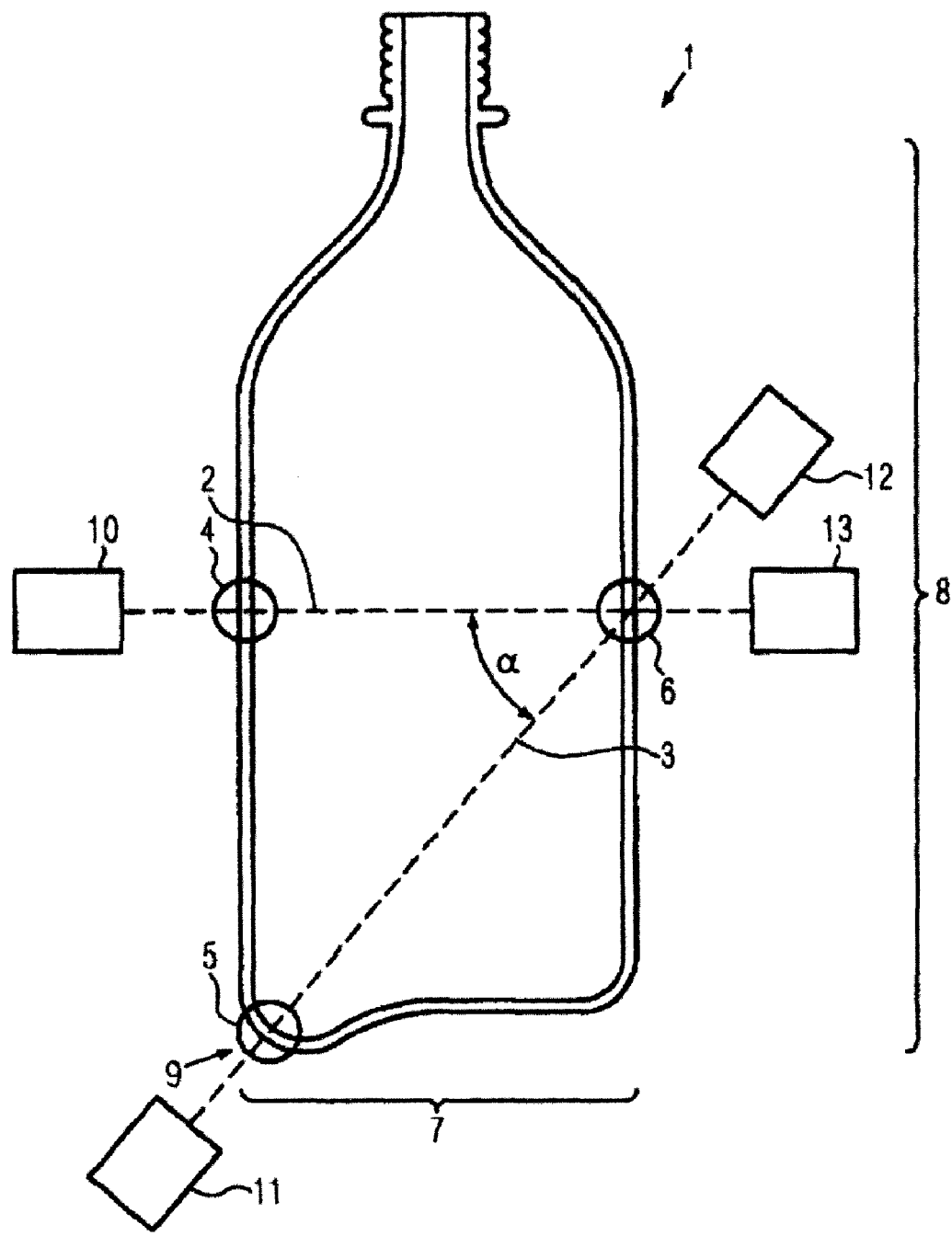
FIG. 1 shows a schematic measurement arrangement in the cross section of the bottle.

FIG. 1 shows a bottle 1. The bottle 1 is in a bottle position in which the wall thickness can be tested. The bottle 1 is made of PET by a blow-molding method.

The bottle 1 has a side-wall area 8 and a bottom area 7. Between the bottom area 7 and the side-wall area 8 there is a transitional area 9. This corresponds to the lower/outer corner/rounded edge of the bottle 1.

Two radiation sources 12, 13 are set up next to the bottle 1. Instead of two radiation sources 12, 13, it is possible to provide only one radiation source if its radiation is divided into two partial beams by a beam splitter or a semitransparent mirror. A movable radiation source, which assumes the positions 12, 13 of the various beam paths in succession, is also possible.

In addition, two detectors 10, 11 are arranged next to or beneath the bottle 1 so that the radiation emitted by the radiation sources 12, 13 can be detected. The detector 10 and the radiation source 13 define the first test path 2 and the detector 11 and the radiation source 12 define the second test path 3.

The absorption at the points of intersection 4, 5, 6 can be deduced from the absorption of the radiation in the points of intersection 4, 5, 6 due to the damping of the radiation.

The points of intersection 4 and 6 are situated approximately at the same height of the bottle 1. Experience has shown that the wall thickness here is therefore approximately the same. By assuming the same wall thickness, the wall thickness of the bottle 1 at the point of intersection 6 can be determined via the test path 2.

With the test path 3 the wall thickness can then be determined in the area of the point of intersection 5 because the absorption in the point of intersection 6 can be subtracted in the calculation. To do so, the longer distance of the test path 3 in the area of the point of intersection 6 can be taken into account due to the inclined position of the test path in comparison with the side wall, and losses due to reflection on the respective interfaces in entrance into and emergence from the container wall at the intersection point 6 may also be taken into account. For the other points of intersection 4, 5 the losses due to reflection at the respective interfaces can also be taken into account.

With the stated measurement setup, the wall thickness in the area of the point of intersection 4 can also be determined with a high precision. To do so, it is assumed that the absorption at the point of intersection 5 is negligible in comparison with the absorption at the point of intersection 6 because the wall thickness here is very thin and the passage through the container wall may optionally occur essentially at a right angle. Therefore, the absorption can be determined in the area of the point of intersection 6, and then with the result of the measurement along the test path 2, absorption in the area of the point of intersection 4 can be determined.

Figure 2A:
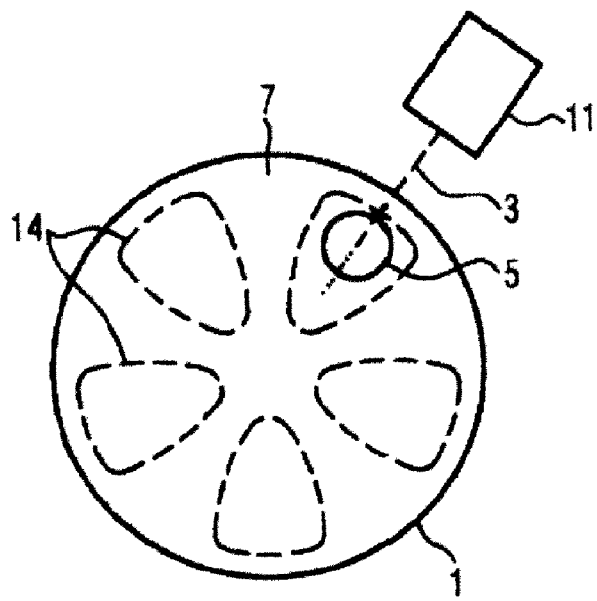
FIG. 2 shows various views of a bottle and a test path in a three-dimensional view.
Figure 2B:
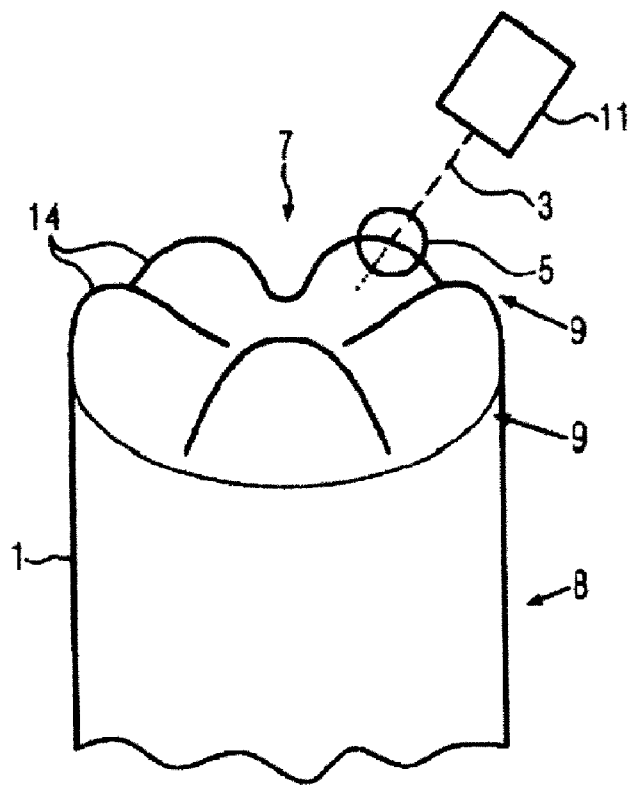

FIG. 2a shows a view of the bottle 1 from underneath. The bottom area 7 is visible here. Various petaloid feet 14 can be seen in the bottom area 7. These feet are formed by outward bulges and allow the bottle to stand securely. FIG. 2b shows a three-dimensional view of the bottom area 7, the side-wall area 8 and the transitional area 9.

Very thin wall thicknesses prevail here due to the fact that the PET material was stretched in blow molding, especially in the areas of the petaloid feet, to adapt it to the corresponding recesses in the blow mold. The point of intersection 5 of the test path 3 with the bottle 1 in the area 9 is therefore preferably in the area of such a petaloid foot 14. This is shown schematically in FIGS. 2a and 2b. The dotted part of the test path 3 should represent the part of the test path 3 running in the cavity of the container 1 while the dashed part represents the part of the test path 3 outside of the container 1.

The invention claimed is:

1. Method for detecting the wall thickness of a plastic bottle, comprising determining the absorption of radiation along a first and a second test path of the measurement radiation, such that the test paths intersect the bottle at two points of intersection, the two test paths each having at least one point of intersection approximately in common, the second test path having a point of intersection in the transitional area of a side-wall area of the bottle in transition to a bottom area of the bottle and, to detect the wall thickness in the transitional area, using the wall thickness that is detected at the common point of intersection.

2. Method according to claim 1, and the first test having a second point of intersection at approximately the same height as the common point of intersection.

3. Method according to claim 1, and the two test paths forming an angle of more than one of 15°, 20°, 30°, 40°, 45°, 50°, 60°, 70° and 80°.

4. Method according to claim 1, and the two test paths forming an angle of less than one of 80°, 70°, 60°, 50°, 45°, 40°, 30°, 20° and 15°.

5. Method according to claim 1, wherein the radiation is electromagnetic radiation such as one of infrared radiation, visible radiation, UV radiation, terahertz radiation, X-ray radiation, radioactive radiation and other particulate radiation.

6. Method according to claim 1, wherein the radiation comprises two different types of radiation.

7. Method according to claim 6, wherein the two different types of radiation comprise electromagnetic radiation of two different wavelengths.

8. Method according to claim 1, and using the value of the wall thickness detected to one of regulate and control a manufacturing process for the bottle.

9. Method according to claim 1, comprising assigning the detected wall thickness of a bottle to one of the blow mold involved in the manufacturing process and the holding mandrel that has transported an injection molding blank for the bottle through a heating station before blow molding, and if necessary, adjusting the production parameters.

10. Method according to claim 9, and wherein the production parameters comprise one of blowing pressure, drawing speed, and temperature profile of the blank.

11. Device for detecting the wall thickness of a plastic bottle, comprising first and second test paths along which the absorption of radiation of the measurement radiation can be determined, the test paths intersecting a bottle position at two points of intersection, and the test paths having at least one point of intersection approximately in common and the second test path having a point of intersection in the transitional area of a side-wall area of the bottle in transition to a bottom area of the bottle and, to detect the wall thickness in the transitional area, using the wall thickness that is detected at the common point of intersection.

12. Method according to claim 11, wherein the plastic bottle is a PET bottle.

13. Method according to claim 1, wherein the plastic bottle is a PET bottle.

* * * * *